US008876696B2

(12) United States Patent
Mikhailenok et al.

(10) Patent No.: US 8,876,696 B2
(45) Date of Patent: Nov. 4, 2014

(54) DEVICE, SYSTEM AND METHOD FOR IMPROVING ERECTILE FUNCTIONS IN MALES

(71) Applicants: Eugene Mikhailenok, San Diego, CA (US); Olga Voronina, San Diego, CA (US)

(72) Inventors: Eugene Mikhailenok, San Diego, CA (US); Olga Voronina, San Diego, CA (US)

(*) Notice: Subject to any disclaimer, the term of this patent is extended or adjusted under 35 U.S.C. 154(b) by 6 days.

(21) Appl. No.: 13/930,768

(22) Filed: Jun. 28, 2013

(65) Prior Publication Data

US 2013/0296963 A1 Nov. 7, 2013

Related U.S. Application Data

(63) Continuation-in-part of application No. 12/713,933, filed on Feb. 26, 2010, now abandoned.

(60) Provisional application No. 61/157,252, filed on Mar. 4, 2009.

(51) Int. Cl.
| | | |
|---|---|---|
| *A61F 5/41* | (2006.01) | |
| *A61N 1/00* | (2006.01) | |
| *A61N 1/36* | (2006.01) | |
| *A61B 5/0488* | (2006.01) | |
| *A61B 5/00* | (2006.01) | |

(52) U.S. Cl.
CPC .............. *A61F 5/41* (2013.01); *A61N 1/36007* (2013.01); *A61B 5/04882* (2013.01); *A61B 5/4393* (2013.01); *A61F 2005/414* (2013.01); *A61B 5/6831* (2013.01); *A61B 5/486* (2013.01)
USPC .............................................. 600/38; 607/143

(58) Field of Classification Search
USPC ...................... 600/38–41; 607/39, 41, 48, 143
See application file for complete search history.

(56) References Cited

U.S. PATENT DOCUMENTS

| | | | |
|---|---|---|---|
| 4,832,033 | A | 5/1989 | Maher et al. |
| 5,411,548 | A | 5/1995 | Carman |
| 5,423,329 | A | 6/1995 | Ergas |
| 5,997,469 | A | 12/1999 | Northcutt |
| 7,519,429 | B2 | 4/2009 | Sawan et al. |
| 7,628,744 | B2 | 12/2009 | Hoffman et al. |
| 7,678,042 | B2 | 3/2010 | Jackson |
| 8,340,786 | B2 | 12/2012 | Gross et al. |
| 2005/0015118 | A1 | 1/2005 | Davis et al. |
| 2010/0016657 | A1 | 1/2010 | Robertson et al. |
| 2010/0076254 | A1 | 3/2010 | Jimenez et al. |

*Primary Examiner* — John Lacyk
(74) *Attorney, Agent, or Firm* — Todd J. Langford; Eric A. Hanscom

(57) ABSTRACT

A device, system and method for improving sexual erectile functions in males that includes an electromyography (EMG) sensor, which is set up in the perineum area over the bulbospongiosus and ischiocavernosus muscles. A cable connects the EMG sensor to an amplifier, the output of which is connected to an analog-to-digital converter. The converter transforms the EMG signal into a form that is accepted by a computer or a smartphone, which contains software that is able to display the EMG signal in a visual-auditory form that can be accepted by the sensory organs of a user. The training of the perineum muscles restricts the blood outflow from the cavernous bodies of a penis and reinforcement of erectile function.

20 Claims, 6 Drawing Sheets

DEVICE, SYSTEM AND METHOD FOR IMPROVING ERECTILE FUNCTIONS IN MALES

CROSS REFERENCE TO RELATED APPLICATIONS

This application is a continuation-in-part of U.S. patent application Ser. No. 12/713,933 filed on Feb. 26, 2010, which in turn claims the benefit of U.S. Provisional Pat. App. No. 61/157,252 filed on Mar. 4, 2009, the entireties of which are hereby incorporated by reference.

STATEMENT REGARDING FEDERALLY SPONSORED RESEARCH OR DEVELOPMENT

This invention was not federally sponsored.

BACKGROUND OF THE INVENTION

Field of the Invention

This invention relates to the general field of devices and methods for the treatment of sexual dysfunctions, and more specifically toward a device for improving erectile functions in males that includes an electromyography (EMG) sensor, which is set up in the perineum area over the bulbospongiosus and ischiocavernosus muscles. A cable connects the EMG sensor to an amplifier, the output of which is connected to an analog-to-digital converter. The converter transforms the EMG signal into a form that is accepted by a computer or a smartphone, which contains software that is able to display the EMG signal in a visual-auditory form that can be accepted by the sensory organs of a user. The proposed device is used for training the muscles of the perineum in order to restrict the blood outflow from the cavernous bodies of a penis and to increase the erectile functions.

Penile erection is a result of increase in blood pressure within cavernous body, which comprises most of the volume inside a penis. It is necessary to mention that the pressure inside the cavernous body depends on the volume of the inflowing blood as well as the volume of the blood leaving the cavernous body over a number of veins, which exist for this specific function (efferent veins).

The volume of the outflowing blood depends on the opening of the arteries activated by the parasympathetic nerves in response to the feeling of sexual excitement. The volume of the inflowing blood level depends on the opening of the veins, a process motivated by the sexual excitement, which, in turn, is controlled by parasympathetic nerves. The volume of the outflowing blood from the cavernous body depends highly on the tension of perineum muscles (bulbospongiosus and ischiocavernosus) located at the base of the cavernous body. When those muscles are tense, they put pressure on the superficial dorsal veins (efferent veins), which are responsible for transporting blood out of the cavernous body. When a male has well-toned perineum muscles then during sexual excitement those muscles have higher effectiveness in pressing up against the veins that stream the blood out of the cavernous body; thus, allowing the blood to stay inside the cavernous body increasing and prolonging the erection.

Under the influence of age and other health issues, the erectile functions weaken. This causes frustration and presents certain risks to any healthy marriage.

Prior art devices exist for exterior use as well as implants for internal use (U.S. Pat. No. 7,678,042, U.S. Pat. No. 5,997, 469, and U.S. Pat. Pub. No. US 2010/0016657). Their function is based on constricting the blood outflow by applying pressure over the soft tissues in the base of a penis with a circular instrument. During this process the outflow of blood is certainly limited; however, such devices also partially limits the inflow of the blood into the cavernous body, which, in turn, weakens the erection. There have been attempts to change the configuration of such devices in order to alleviate the problem of blocking the blood inflow; however, those attempts have only partially solved the problem. The reason for that is because the vessels that transport the blood in and out of the cavernous body run on the inside as well as on the outside of the penis. The device that is acting from the exterior is only able to apply pressure on the veins that are located on the outside of the cavernous body but not on those located inside the penis.

Another problem that is associated with these devices and methods is that the above-mentioned instruments can prolong the erection when they are put on after the penis is already erect and they are designed to put significant pressure on the cavernous body at the base of a penis from the outside. With such method there is an obvious risk of damaging the soft tissues of a penis due to a prolonged restriction in the blood flow.

The solutions that use implants are much more effective as the implants are installed specifically around the veins. Their shortcoming is that those sorts of methods can be traumatic due to the surgical procedures that must take place. Those methods are only used in rare cases and on patients with serious medical condition. There are also other risks associated with surgical methods, such as post-surgical difficulties. Thus, mass application of implants is not viable.

There are a number of devices for the electric stimulation of muscles. They use sensors (for example, electrodes) mounted on the skin surface, such as those disclosed in U.S. Pat. Pub. No. 2005/0015118 and U.S. Pat. No. 4,832,033) or get implanted into a muscle or a nerve, such as those disclosed in U.S. Pat. No. 7,519,429 and U.S. Pat. Pub. No. 2010/ 0076254). Their function is based on muscle contraction under the influence of electrical current. This design functions under the assumption that the artificial and unnatural imitation of muscle contraction would lead to the same processes within the muscle cells (myocites) as the natural muscle contraction, which is biologically controlled by the activation of polyenergetic synaptic impulses that pass throughout the muscle nerves. It is true that the electrical impulse leads to a mechanical muscle contraction as it leads to the internal cellular energy expenditure. With that in mind, although the muscle is contracted, it does not lead to the notable change in synthesis of the muscle proteins (actin and myosin), which are responsible for the reinforcement of the muscle contraction strength. The synthesis of those proteins takes place exclusively due to the natural muscle activation initiated by natural synaptic input. That synaptic input activates a cascade of chemical reactions that free up the process of protein synthesis within muscle cells. This is the main reason why in sports, where higher muscle strength and tonus are required, natural muscle training is used as opposed to electrical muscle stimulation.

Apart from the aforementioned, the prior art has little if any teachings in the field of electrical muscle stimulation aimed at bulbospongiosus and ischiocavernosus muscles in males. The choice among these types of devices is limited to the applications for the perineum muscles in women and the electric stimulation of the anal sphincter. In part the above is explained by the specifics of male perineum anatomy. The bulbospongiosus and ischiocavernosus muscles are fairly small and are located under a thick layer of fat tissue. This renders the electrical stimulation devices operating through the skin surface ineffective due to the broad activation of the diaphragma pelvis muscle complex.

Biofeedback training methods are based on registering the EMG signal from muscles with the use of specialized sensors (electrodes) and the conversion of the acquired EMG signal data into a form that is easy for the final user to comprehend. This sensory signal (also known as biofeedback signal) gets converted into a form of auditory, visual, tactile, pain or any other stimulus that informs the user (the trainee) about the current state of their muscle activity. The advantage of the biofeedback method is that it presents objective and accurate information about the processes which take place inside the body of a user which otherwise would not be picked up by the natural sensory organs. Due to the fact that perineum bulbospongiosus and ischiocavernosus muscles are not under the conscious control of a trainee, the activation of those muscles for training purposes without the use of biofeedback technologies is difficult and ineffective.

There are prior art disclosures that utilize a biofeedback method for training the perineum muscles. These methods rely on pressure sensors positioned inside vaginal cavity or inside rectum, such as in U.S. Pat. No. 7,628,744. They also rely on EMG sensors positioned near the vaginal or rectal muscles. The use of EMG sensors is more advantageous as they reflect the actual activity of a particular muscle where the pressure sensor gets affected by the activity of the stomach, hips, and diaphragm, rather than exclusively by the perineum muscles.

There are a number of EMG-biofeedback devices for training the bulbospongiosus and ischiocavernosus muscles in females and also for the muscles of anal sphincter, such as those in U.S. Pat. No. 8,340,786, U.S. Pat. No. 5,411,548, and U.S. Pat. No. 5,423,329 and others. That being said, these references do not teach EMG-biofeedback devices aimed at training the bulbospongiosus and ischiocavernosus muscles in males. The devices for training bulbospongiosus and ischiocavernosus muscles in females cannot be applied to males. The reason is that the sensor is designed for the insertion inside the vaginal cavity and registers the signal exclusively from muscles located along the sidewalls of inner space of vaginal cavity.

The device we are offering allows registering EMG-signal from the bulbospongiosus and ischiocavernosus muscles in males due to the sensor which we have developed for this particular purpose (see below). With our design the signal gets registered exclusively from bulbospongiosus and ischiocavernosus muscles without picking up the signal from the surrounding muscles like the anal sphincter.

Thus there has existed a long-felt need for a device and method for overcoming male sexual disorders and improving sexual functions in males.

SUMMARY OF THE INVENTION

The current invention provides just such a solution by having a device for improving sexual functions in males that includes an electromyography (EMG) sensor, which gets set up in the perineum area over the bulbospongiosus and ischiocavernosus muscles. A cable connects the EMG sensor to an amplifier, the output of which is connected to an analog-to-digital converter. The converter transforms the EMG signal into a form that is accepted by a computer or a smartphone, which contains specialized software that is able to display the EMG signal in a visual-auditory form that can be accepted by the sensory organs of a user.

A goal of the current invention is to create a device for use by males to overcome the above referred, naturally occurring sexual dysfunction regardless of whether the condition is of a temporary or permanent period. To meet this goal, a particular embodiment of the current disclosure provides a device, which by increasing the perineum muscle tone, specifically by increasing the tone and the endurance of the bulbospongiosus and ischiocavernosus muscles, affects the circulation of the blood in a manner that, in effect, impedes the blood outflow from the cavernous body of a penis.

Periodic and intensive tension is required in order to train any muscle. The muscles of perineum, including the bulbospongiosus and ischiocavernosus, are not naturally designed to be controlled by a conscious cognitive process, unlike the skeletal muscles of legs and hands. The perineum muscles are designed to perform actions that are not tied to the conscious decision making process, like the processes of defecation, urination and sexual functions. Thus, the attempts to train the perineum muscles by relying on conscious efforts to flex those muscles without the objective control and reference would not yield any notable results in most males. Thus, a major purpose of the device, system, and method disclosed herein is to create an objective reference that informs an individual about the state of tension or relaxation of perineum muscles in real time.

Due to the location of the bulbospongiosus and ischiocavernosus muscles, the cutaneous electrodes that are normally used for registering an EMG signal cannot register such a signal precisely and reliably. Therefore, one of the goals of the discussed invention was to develop an EMG sensor, which would be optimally designed to register an EMG signal from the muscles of perineum in males.

The functions of bulbospongiosus and ischiocavernosus muscles are very selective when it comes to outflow of the blood from the cavernous body as this is their key function. The tension of bulbospongiosus and ischiocavernosus muscles limit the outflow exclusively to the veins that carry the blood out of the cavernous body without affecting the arterial blood flow bringing the blood into the cavernous body. Furthermore, the training of bulbospongiosus and ischiocavernosus muscles to increase their tonus, strength, volume, and endurance is a natural procedure that has little or no negative effects on the user of the current device, system, and method, regardless of age or the overall physical condition.

An advantage of the device, system and method disclosed herein is that the training of bulbospongiosus and ischiocavernosus muscles engages the physiological mechanism for synthesis of the specific contractile proteins. This mechanism is responsible for the natural growth, increase in tone, contracting ability, and endurance of the perineum muscles. Apart from that, the invention disclosed herein allows training the muscles by positioning the sensor such that it can read EMG signals specifically from bulbospongiosus and ischiocavernosus muscles and provide the user with feedback of the activity from those particular muscles.

The current invention also differs from the other biofeedback devices by its operating mode, which aims specifically at the training of the toning efforts that are most viable for increasing the tonus, strength, and endurance of bulbospongiosus and ischiocavernosus muscles. In turn this directly affects the erectile function of a penis.

It is an object of the invention to provide a device, system, and method for improving sexual erectile functions in males.

It is another object of the invention to provide a device, system, and method for strengthening and toning the bulbospongiosus and ischiocavernosus muscles of a male user.

It is a further object of this invention to provide a device, system, and method that have little or no negative effects on the user.

The device, system and method disclosed herein are not focused on training the muscles of the anal sphincter. Although these muscles are a part of perineum muscles, training the muscles of anal sphincter is not pertinent to our solution. Anal sphincter muscles also have a different purpose and do not relate to the erectile functions.

There has thus been outlined, rather broadly, the more important features of the invention in order that the detailed description thereof may be better understood, and in order that the present contribution to the art may be better appreciated. There are additional features of the invention that will be described hereinafter and which will form the subject matter of the claims appended hereto. The features listed herein and other features, aspects and advantages of the present invention will become better understood with reference to the following description and appended claims.

BRIEF DESCRIPTION OF THE FIGURES

The accompanying drawings, which are incorporated in and form a part of this specification, illustrate embodiments of the invention and together with the description, serve to explain the principles of this invention.

DETAILED DESCRIPTION OF THE INVENTION

Figure 1:
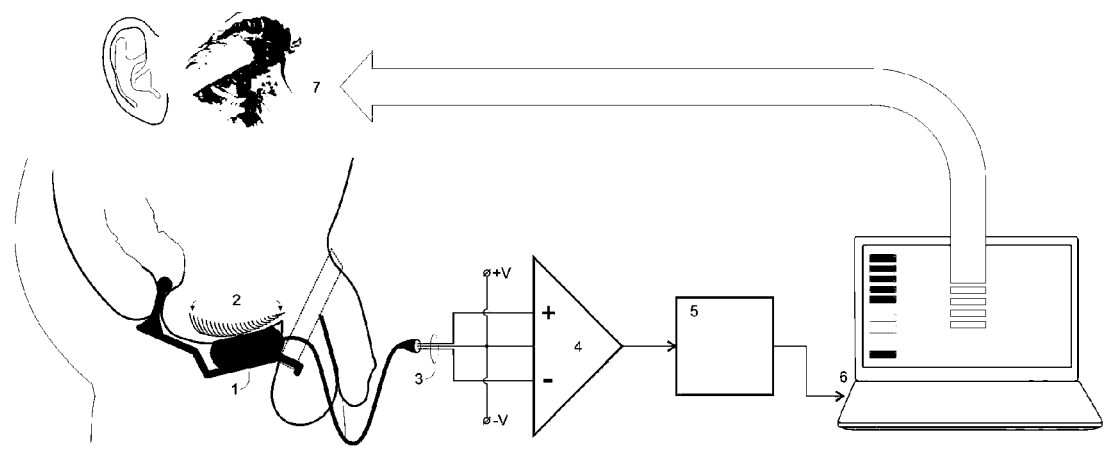
FIG. 1 is a schematic view of a system for improving sexual functions in males according to selected embodiments of the current disclosure.

Many aspects of the invention can be better understood with the references made to the drawings below. The components in the drawings are not necessarily drawn to scale. Instead, emphasis is placed upon clearly illustrating the components of the present invention. Moreover, like reference numerals designate corresponding parts through the several views in the drawings.

FIG. 1 is a schematic view of a system for improving sexual functions in males according to selected embodiments of the current disclosure. The device for improving sexual erectile functions in males includes an EMG-sensor 1, which gets set up in the perineum area over the bulbospongiosus and ischiocavernosus muscles 2. A cable 3 connects the EMG-sensor to an amplifier 4. The signal generated by the amplifier is sent to an analog-to-digital converter 5. The converter transforms the EMG signal into a form that is accepted by a computer or a smartphone 6, which contains specialized software that is able to display the EMG signal in a visual-auditory form that can be accepted by the sensory organs of a user 7.

Figure 2:
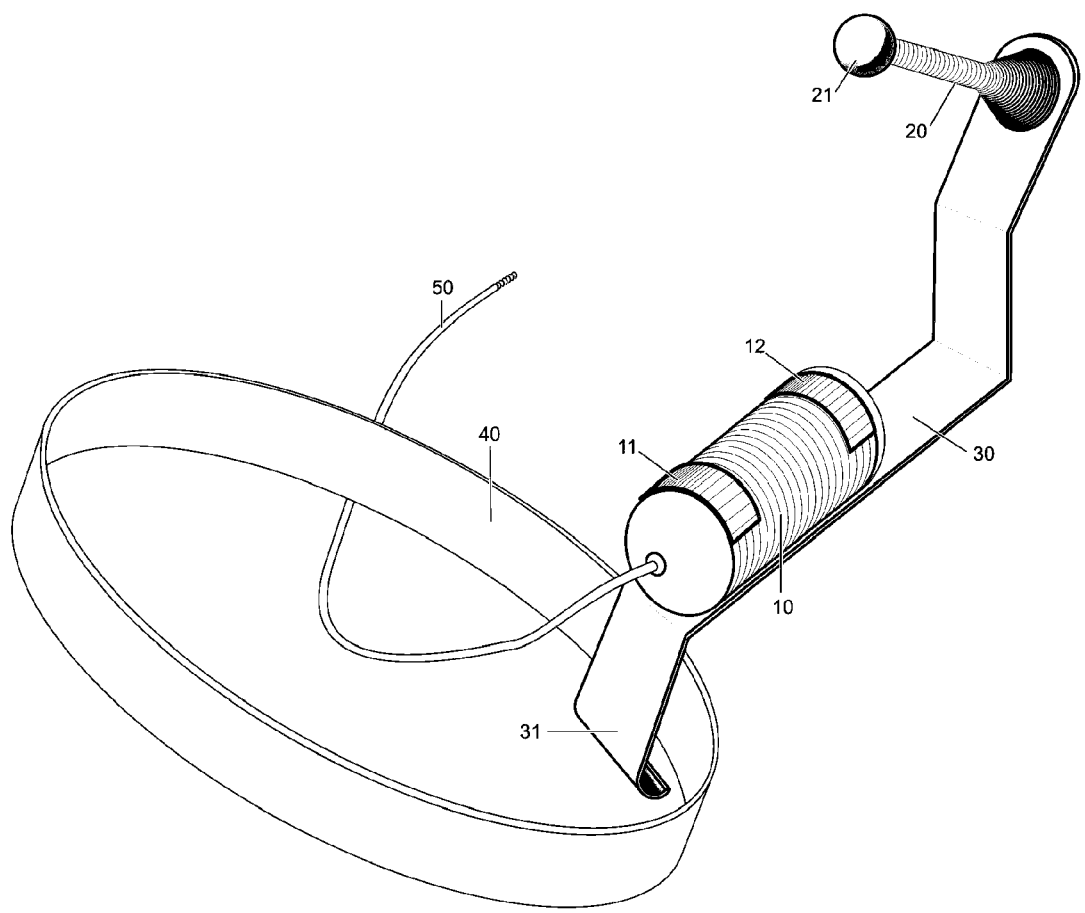
FIG. 2 is a sensor for registering an EMG signal according to selected embodiments of the current disclosure.

FIG. 2 is a sensor for registering an EMG signal according to selected embodiments of the current disclosure. The sensor for registering the EMG signal from bulbospongiosus and ischiocavernosus muscles in males includes a registering electrode 10, a reference electrode, a bridging plate 30, a fixating belt 40, and an electrical cable 50. The registering electrode 10 has a cylindrical shape and is two and one-half (2½) inches long and one and one-half (1½) inches in diameter, featuring dual contact surfaces 11, 12 on each of the edges made out of an electro conductive, biologically inert material, one-quarter (¼) inches in width and one-third (⅓) of the perimeter of the electrode in length each. A reference electrode has two parts: a foundation of cylindrical shape 20 and a contact section 21. The foundation of cylindrical shape 20 is one-quarter (¼) inches in diameter, two (2) inches in length widening at its base to firmly connect to the bridging plate. The contact section 21 of the reference electrode, which is a spherical shape that is one-half (½) inches in diameter, is made out of an electro conductive, biologically inert material. The bridging plate 30 is made out of a non-conductive material that serves for connecting the registering electrode and the reference electrode, and features a shoulder 31 at its front end, which is designed to hold the fixating belt. The fixating belt 40 holds and presses the sensor against the perineum and is fixed at the end of the bridging plate with its lower side. Its upper side stretches and fixates over the penis in the share bone region. The electrical cable 50 is for connecting the contact surfaces of registering and reference electrodes with an external component, such as the EMG-amplifier.

Figure 3:
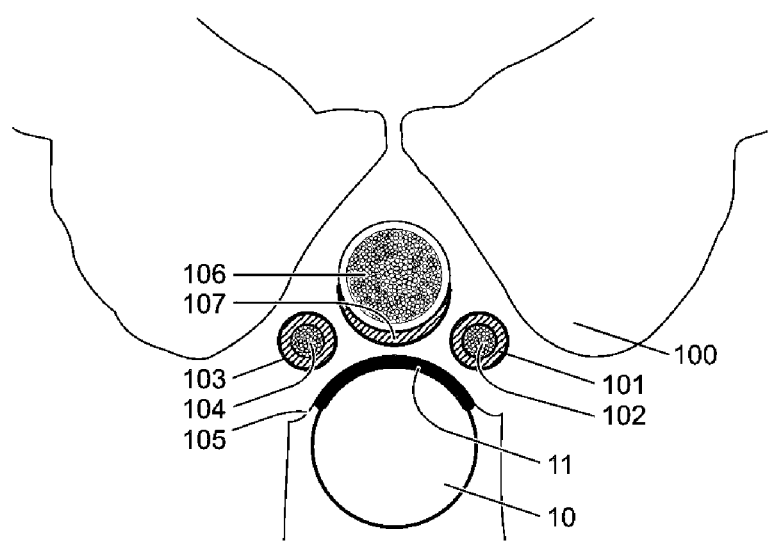
FIG. 3 is a projection view of the male perineum muscles in relation to a registering electrode according to selected embodiments of the current disclosure.

FIG. 3 is a projection view of the male perineum muscles in relation to a registering electrode according to selected embodiments of the current disclosure. The registering electrode 10 is show with a front contact surface 11. Site bones 100 are next to the left and right ischiocavernosus muscles 101 and 103, which surround the left and right legs of the cavernous body 102 and 104 (Crus penis). The perineum skin 105 is in contact with the front contact surface 11. The bulbospongiosus muscle 107 is proximate to the penis bulb 106.

The convex cylindrical shape of the registering electrode is chosen due to its ability to come in contact with the maximum area of the skin surface within the perineum, which, in turn, improves the quality of the weak registered signal from the muscles located deep inside the perineum. Furthermore, the projection of bulbospongiosus and ischiocavernosus muscles onto the skin of the perineum, makes this shape of the sensor optimal for registering the EMG signal from both of the muscles at the same time. One of the critical functions for getting clean EMG signals from the bulbospongiosus and ischiocavernosus muscles is tight fixation of the sensor against the skin of the perineum. This is ensured with the fixating belt, which tension force pushes the sensor in forward and in an upward direction simultaneously, because of the way it is routed over the base of a penis.

The referenced electrode, which is connected to the midpoint of the amplifier power supply (as shown in FIG. 1) gets inserted inside the anal canal so that its spherical contact sensor is located above the internal anal sphincter. Such a position for the reference electrode provides a low-resistance contact with the body of a user as the mucus coat inside the rectum is moist and provides high electric conductivity. It is also electrically connected with other organs in the human body that together make up a large area. This creates the possibility for registering the EMG signal from the bulbospongiosus and ischiocavernosus muscles with a minimal amount of noise. Such a setup for the reference electrode also minimizes the electrical field from the activity of the anal sphincter muscles, which, in turn improves the quality of the EMG signal that is registered from the bulbospongiosus and ischiocavernosus muscles. Another important advantage for the location of the reference electrode is that it serves as an additional fixation point for the EMG sensor as the tonus of the sphincter muscles securely holds the referenced electrode as well as the overall sensor assembly in place and resists movement.

The bridging plate, in a particular embodiment, is made out of flexible plastic and has a curved shape as displayed in FIG. 2. That shape permits the placement of the registering electrode and the referenced electrodes at the appropriate sections of the male perineum.

The electromyographic signal that is registered with EMG-sensor from the bulbospongiosus and ischiocavernosus muscles has been found to have an amplitude of no more than 15-20 μv (microvolts) when those muscles are tense. For that reason an amplifier is used with the amplification coefficient of 105 in the 20-500 Hz frequency range.

In order to convert the analog signal at the amplifier output into a digital form, which then gets routed into a computer, a 10-bit analog-to-digital converter (ADC) is used with no less than 1 kHz sampling rate. The output of the ADC is connected to a USB port of a computer or an analogous port on other electronic devices. That same port may be used to power the electrical components of the device. As one will appreciate, a smart phone may be used in place of a personal computer, and as such is treated as a form of a computer herein. Further, alternative means of transferring data between the ADC to the computer is contemplated, including wireless connections such as Bluetooth WiFi™ based on based on the Institute of Electrical and Electronics Engineers (IEEE) 802.11 standards.

The computer is set up with software specifically designed to reflect the objective: quantitative audio-visual information about the integrated EMG signal directly reflecting the tension of the bulbospongiosus and ischiocavernosus muscles. The software proves the signal from the ADC and provides additional information for a user in a form of a graphical representation of timing and amplitudes of reference charts, which serve as a goal that a user needs to reach in order to improve the function of his perineum muscles.

Figure 4:
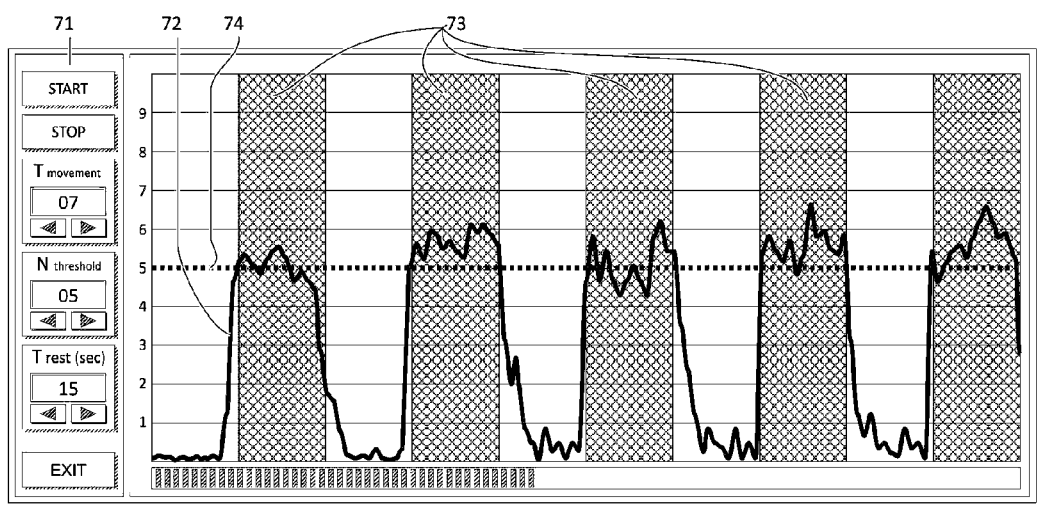
FIG. 4 is a graphical user interface for a first training session of computer software according to selected embodiments of the current disclosure.

FIG. 4 is a graphical user interface for a first training session of computer software according to selected embodiments of the current disclosure. The procedure of working with the device features the steps discussed below.

First, set up and attach the EMG sensor in the perineum of a user. The correct user position is sitting in a chair with soft padding. Connect the sensor cable to the EMG signal amplifier. Connect the ADC output to a computer. Turn on the computer and launch the software designed to work with the device.

Second, the user performs the training session that includes two sections. The goal of the first part of the session includes frequent, brief (such as five (5) to seven (7) seconds) phases of bulbospongiosus and ischiocavernosus muscles flexes with maximum possible power. During the exercise, a user refers to the time 73 and the amplitude 74 criteria marks on a screen connected with or integrated into the computer in order to control the tension of his own perineum muscles in duration and flexing power. The graph, which reflects the muscle activity, is shown on the screen in a form of "integrated EMG" or "iEMG" 72, which shows the result of full-wave rectification of a raw EMG signal after its low pass filtration (5 Hz). The criteria by which the duration of the muscle flexing is referenced is presented by colored vertical lines 73, the width of which corresponds with the length of the muscle flexing duration. A user (trainee) should flex his muscles while the graph is passing over those lines 72. The criteria by which the power of the muscle flex is judged is referenced by an amplitude threshold 74—a horizontal line, which a user needs to get close to by flexing his muscles as hard as he can. This method of "threshold" biofeedback is optimal for training muscles under conscious controlled flexing.

Figure 5:
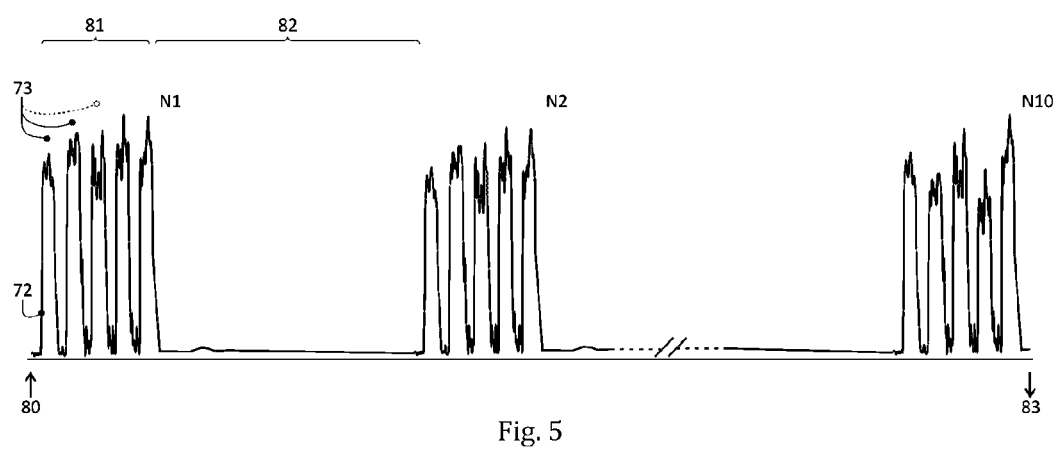
FIG. 5 is a graph showing the timing of a first training session according to selected embodiments of the current disclosure.

FIG. 5 is a graph showing the timing of a first training session according to selected embodiments of the current disclosure. This first part of a training session includes ten (10) cycles of muscle flexing (N1 to N10), each of them having five (5) consequent muscle flexes 81, separated by periods of rest 82 that range from fifteen (15) to sixty (60) seconds, which occur between the starting point of the first part training session 80 and the ending point of the first part of the training session 83. The software prompts the user on the timed, consecutive cycles of muscle flexes. The software utilizes the sound, speech and visual stimulus as well as textual information on the screen or communicates it through loudspeakers. The software allows the user to adjust the time and the flexing force parameters of the training session based on individual abilities of a user. For that purpose, on the left side of the graphical interface of the software (as shown in FIG. 4) there is an area 71 enabled the adjustment of the time (for how long a user needs to flex his muscles), the threshold (responsible for the power of the muscle flexing), and the rest time between the muscle flexes. The first part of the session ends when all of 10 cycles have been completed or when a user is tired and stops the session before its completion.

Figure 6:
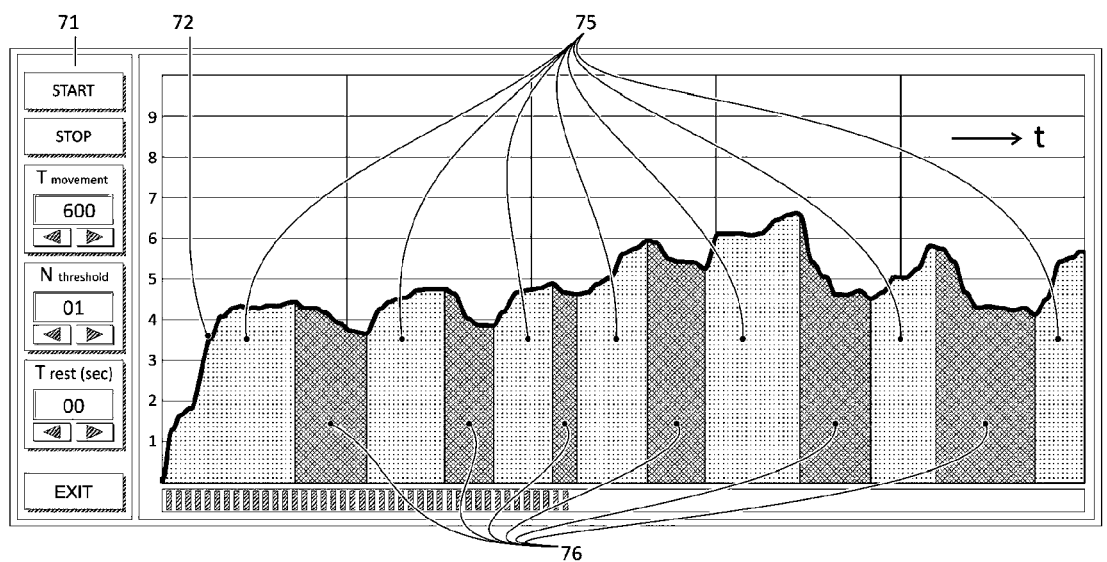
FIG. 6 is a graphical user interface for a second training session of computer software according to selected embodiments of the current disclosure.

FIG. 6 is a graphical user interface for a second training session of computer software according to selected embodiments of the current disclosure. The upward moving phases of iEMG 75 demonstrate the increase in muscle flex and associate with engaging a motivational biofeedback signal (such as a multimedia file featuring erotic content). The downward moving phases of iEMG 76 demonstrate the decrease in muscle tension and associate with disengaging a motivational biofeedback signal.

The second section or part of the session is responsible for two goals. The first goal is developing the endurance of the perineum muscles allowing the prolonged tension. The second goal is the connection and association of bulbospongiosus and ischiocavernosus muscle tension with the feeling of the erotic excitement. The latter is essential in order for bulbospongiosus and ischiocavernosus muscles to tense not only under the physical, conscious control, but also unconsciously under erotic excitement, which would result in more powerful and prolonged erections.

The training procedure taking place in the second part of the training session involves prolonged flexing of bulbospongiosus and ischiocavernosus muscles. Differentiated from the numerous flexes of the perineum muscles we described in the first part of the session, the prolonged tension of the bulbospongiosus and ischiocavernosus muscles require the user to get over a number of negative emotions. This task is solved by the proposed device with the use of audio-visual, erotic multimedia content (video movies and illustrations) as a means of biofeedback. The ability or inability of watching a video film is firstly determined by the sign of the first derivative of iEMG: with the increase in tension/flex of perineum muscles, the video screen is on. With the decrease of muscular tension, the screen turns off. This form of biofeedback contains clear positive reinforcement qualities and is able to compensate for the negative emotions motivating a user to make an extra effort in order to keep up the tension of his perineum muscles; thus, prolonging the time of the motivational positive erotic reinforcement.

The use of the above form of biofeedback, featuring erotic content, also covers the second goal of this training session, which, as mentioned earlier, makes the association between the flexing of bulbospongiosus and ischiocavernosus muscles and the erotic excitement brought out by the demonstration of erotic multimedia content. During the session, the brain forms associative, neurological connections between the state of erotic excitement and the higher tonus of the perineum muscles relying on the mechanisms of conditioned reflex. The numerous repetitions of this association forms a stable, unconscious form of behavior in which the perineum muscles would flex in response to the feeling of the erotic excitement, thereby making the erection longer and more powerful.

A significant differentiating feature of the proposed device, system, and method is the use of the motivational biofeedback signal in the second part of the training session and specifically the use of the first positive derivative of the iEMG signal graph.

It is known that the speed and the stability of conditioned reflex depends on synchronization of the conditioned and unconditioned stimuli. During the procedures that take place in the second part of the training session, the erotic multimedia files represent the unconditioned stimulus, which activates the physiological mechanism of erotic excitement. The conditioned stimulus is represented by the tension of bulbospongiosus and ischiocavernosus muscles. To be specific, it is represented by the physical flow of afferent impulses from the movement receptors of those muscles. It is known that the movement receptors send the signals reflecting the changes in muscle tension into the brain and not the signals reflecting the strength of the tension. Therefore, the information about the muscle tension is received by the brain in a form of first derivative of the muscle tension strength. This is the reason why during the second part of the training session our device provides the unconditioned stimulus together with the increase in the perineum muscle tension when the first derivative is positive. This way, the neural processes, launched by the conditioned and unconditioned stimuli synchronize. This leads to the rapid formation of a stable unconditioned reflex.

The second part of the training session usually takes ten (10) minutes. In some cases it takes less time if a user gets tired and decides to stop the training session. It has been found that a total number of twenty (20) training sessions is needed to get the desired effect of increase in erectile function, though more or less may be performed depending on a users specific circumstances. In a particular embodiment, the minimal interval between consecutive sessions is four (4) hours, while the maximal interval is three (3) days.

It should be understood that while the preferred embodiments of the invention are described in some detail herein, the present disclosure is made by way of example only and that variations and changes thereto are possible without departing from the subject matter coming within the scope of the following claims, and a reasonable equivalency thereof, which claims I regard as my invention.

That which is claimed:

1. A device comprising
a registering electrode, a reference electrode, a bridging plate, and a fixating belt,
where the registering electrode comprises dual contact surfaces,
where the reference electrode comprises a foundation and a contact section,
where the bridging plate is made from a non-conductive material, where the bridging plate physically connects the registering electrode to the reference electrode,
where the fixating belt is secured to an end of the bridging plate, where the fixating belt fixates over the base of the penis of a user and causes the registering electrode to press against the perineum of the user when in use.

2. The device of claim 1, further comprising an electrical cable, where the electrical cable provides an electrical connection from the dual contact surfaces of the registering electrode and the contact section of the reference electrode to an external component.

3. The device of claim 1, where the foundation of the referenced electrode has a cylindrical shape.

4. The device of claim 1, where the contact section of the reference electrode has a spherical shape.

5. The device of claim 1, where the contact section of the reference electrode comprises an electro-conductive, biologically inert material.

6. The device of claim 1, where the registering electrode has a cylindrical shape.

7. A system comprising
a sensor for registering an electromyographic signal, an amplifier, and an analog-to-digital converter;
where the sensor for registering an electromyographic signal provides an electromyographic signal, where the sensor for registering an electromyographic signal comprises a registering electrode, a reference electrode, a bridging plate, and a fixating belt, where the registering electrode comprises dual contact surfaces, where the reference electrode comprises a foundation and a contact section, where the bridging plate is made from a non-conductive material, where the bridging plate physically connects the registering electrode to the reference electrode, where the fixating belt is secured to an end of the bridging plate, where the fixating belt causes the registering electrode to press against the perineum of a user when in use;
where the amplifier amplifies the signal provided by the sensor for registering an electromyographic signal; and
where the analog-to-digital converter converts signal amplified signal from the amplifier to a digital form.

8. The system of claim 7, further comprising a computer, where the computer comprises software for processing the signal from the analog-to-digital converter.

9. The system of claim 8, wherein the computer further comprises a screen, where the screen displays quantitative information about the signal from the analog-to-digital converter, whereby the quantitative information reflects the tension of the bulbospongiosus and ischiocavernosus muscles.

10. The system of claim 8, wherein the computer is a smart phone.

11. The system of claim 7, where the sensor for registering an electromyographic signal further comprising an electrical cable, where the electrical cable provides an electrical connection from the dual contact surfaces of the registering electrode and the contact section of the reference electrode to the amplifier.

12. The system of claim 7, where the registering electrode has a cylindrical shape.

13. The system of claim 7, where the foundation of the referenced electrode has a cylindrical shape.

14. The system of claim 7, where the contact section of the reference electrode has a spherical shape.

15. A method for improving sexual erectile functions in males comprising the steps of
securing a sensor for registering an electromyographic signal to a user, where the sensor for registering an electromyographic signal provides an electromyographic signal, where the sensor for registering an electromyographic signal comprises a registering electrode, a reference electrode, a bridging plate, and a fixating belt, where the registering electrode comprises dual contact surfaces, where the reference electrode comprises a foundation and a contact section, where the bridging plate is made from a non-conductive material, where the bridging plate physically connects the registering electrode to the reference electrode, where the fixating belt is secured to an end of the bridging plate, where the fixating belt causes the registering electrode to press against the perineum of a user when in use;

connecting the sensor for registering an electromyographic signal to a computer; and performing a training session, where the training session comprises flexing and resting the bulbospongiosus and ischiocavernosus muscles of a user.

16. The method of claim 15, wherein connecting the sensor for registering an electromyographic signal to a computer comprises connecting the sensor for registering an electromyographic signal to an amplifier;

connecting the amplifier to an analog-to-digital converter; and connecting the analog-to-digital converter to the computer.

17. The method of claim 16, where the sensor for registering an electromyographic signal further comprising an electrical cable, where the electrical cable provides an electrical connection from the dual contact surfaces of the registering electrode and the contact section of the reference electrode to the amplifier.

18. The method of claim 15, wherein the training session comprises ten muscle-flexing cycles, where each muscle flexing cycle comprises five muscle flexes separated by periods of rest.

19. The method of claim 15, wherein the training session comprises prolonged flexing of bulbospongiosus and ischiocavernosus muscle, where the computer provides erotic multimedia content to the user when there is in increase in flexing of the bulbospongiosus and ischiocavernosus muscles, where the computer does not provide erotic multimedia content to the user when there is a decrease in flexing of the bulbospongiosus and ischiocavernosus muscles.

20. The method of claim 15, where the computer comprises software for processing the signal from the sensor for registering an electromyographic signal, where the computer further comprises a screen, where the screen displays quantitative information about the signal from the sensor for registering an electromyographic signal, whereby the quantitative information reflects the tension of the bulbospongiosus and ischiocavernosus muscles.

* * * * *